(12) United States Patent
Kool

(10) Patent No.: US 10,428,316 B2
(45) Date of Patent: Oct. 1, 2019

(54) IMMORTALISED CHICKEN EMBRYO FIBROBLASTS

(71) Applicant: Intervet Inc., Madison, NJ (US)

(72) Inventor: Jaap Kool, Münster (DE)

(73) Assignee: Intervet Inc., Madison, NJ (US)

( * ) Notice: Subject to any disclaimer, the term of this patent is extended or adjusted under 35 U.S.C. 154(b) by 88 days.

(21) Appl. No.: 15/532,189

(22) PCT Filed: Dec. 3, 2015

(86) PCT No.: PCT/EP2015/078457
§ 371 (c)(1),
(2) Date: Jun. 1, 2017

(87) PCT Pub. No.: WO2016/087560
PCT Pub. Date: Jun. 9, 2016

(65) Prior Publication Data
US 2018/0171309 A1   Jun. 21, 2018

(30) Foreign Application Priority Data

Dec. 4, 2014   (EP) .................................... 14196345

(51) Int. Cl.
| | | |
|---|---|---|
| C12N 7/00 | (2006.01) | |
| C12N 7/08 | (2006.01) | |
| A61K 39/12 | (2006.01) | |
| C12N 7/02 | (2006.01) | |
| C12N 15/79 | (2006.01) | |

(52) U.S. Cl.
CPC ............... *C12N 7/08* (2013.01); *A61K 39/12* (2013.01); *C12N 7/00* (2013.01); *C12N 7/02* (2013.01); *C12N 15/79* (2013.01); *C12N 2330/51* (2013.01); *C12N 2510/02* (2013.01); *C12N 2510/04* (2013.01); *C12N 2710/16034* (2013.01); *C12N 2710/16351* (2013.01)

(58) Field of Classification Search
None
See application file for complete search history.

(56) References Cited

U.S. PATENT DOCUMENTS

| | | | |
|---|---|---|---|
| 2001/0016348 A1 | 8/2001 | Bouquet et al. | |
| 2008/0227146 A1 | 9/2008 | Sandig et al. | |
| 2014/0363467 A1* | 12/2014 | Stice et al. ........... | C12N 5/0696 424/209.1 |

FOREIGN PATENT DOCUMENTS

| | | |
|---|---|---|
| EP | 1685243 B1 | 6/2008 |
| JP | 2007236311 A | 9/2007 |
| WO | 9744443 A1 | 11/1997 |
| WO | 9806824 A1 | 2/1998 |
| WO | 2005042728 A2 | 5/2005 |
| WO | 2005100546 A1 | 10/2005 |
| WO | 2007077256 A1 | 7/2007 |
| WO | 2007077256 B1 | 10/2007 |
| WO | 2009004016 A1 | 1/2009 |
| WO | 2010083841 A2 | 7/2010 |

OTHER PUBLICATIONS

Campisi, J., From cells to organisms: can we learn about aging from cells in culture?, Experimental Gerontology, 2001, pp. 607-618, 36.

Christman, S.A. et al., Contributions of differential p53 expression in the spontaneous immortalization of a chicken embryo fibroblast cell line, BMC Cell Biology, Published: Jun. 30, 2006, doi: 10.1186/1471-2121-7-27, 7:27.

Christman, S.A. et al., Modulation of p53 expression and its rile in the conversion to a fully immortalized chicken embryo fibroblast line, FEBS Letters, 2005, pp. 6705-6715, 579.

Darimont, Christian, et al., SV40 T antigen and telomerase are required to obtain immortalized human adult bone cells without loss of the differentiated phenotype, Cell Growth & Differentiation, Feb. 2002, pp. 59-67, vol. 13.

Database WPI/Thomson, Week 201341, AN2013-G00202, XP002739443, (2013).

Deepika Ahuja et al, SV40 large T antigen targets multiple cellular pathways to elicit cellular transformation, Oncogene, 2005, pp. 7729-7745, 24.

European Search report for EP14196345.4 dated May 22, 2015, 9 pages.

Himly, M. et al., The DF-1 chicken fibroblast cell line: transformation induced by diverse oncogenes and cell death resulting from infection by avian leukosis viruses, Virology, 1998, pp. 295-304, 248.

International Search Report for PCT/EP2015/078457, dated Mar. 2, 2016, 15 pages.

Ivics, Z. and Izsvak, Z., The expanding universe of transposon technologies for gene and cell engineering, Mobile DNA 2010, pp. 25-39, 1.

Kim, S-H., et al., Upregulation of chicken p15INK4b at senescence and in the developing brain, Journal of Cell Science, 2006, pp. 2435-2443, 119.

Kong, B.-W., et al., Application of the sleeping beauty transposon system to avian cells, Animal Genetics, 2008, pp. 180-186, 39.

Michailidis, G. et al., Endogenous and ectopic expression of telomere regulating genes in chicken embryonic fibroblasts, Biochemical and Biophysical Research Communications, 2005, pp. 240-246, 335.

Miyazaki, J. et al., Expression vector system based on the chicken B-actin promoter directs efficient production of interleukin-5, Gene, 1989, pp. 269-277, 79.

Niwa, H. et al., Efficient election for high-expression transfectants with a novel eukaryotic vector, Gene, 1991, pp. 193-200, 108.

Rekha, K. et al., Growth and replication of infectious bursal disease virus in the DF-1 cell line and chicken embryo fibroblasts, Hindawi Publishing Corporation, Published May 14, 2014, Article ID 494835, 6 Pages, vol. 2014.

(Continued)

*Primary Examiner* — Catherine S Hibbert

(57) ABSTRACT

The present invention relates to immortalized chicken embryo fibroblasts, to cell cultures comprising such immortalized cells, to vaccines comprising such cells, to methods for the propagation of avian viruses on such cells, and to methods for the preparation of such cells and such vaccines.

18 Claims, 6 Drawing Sheets

Figure 1A:
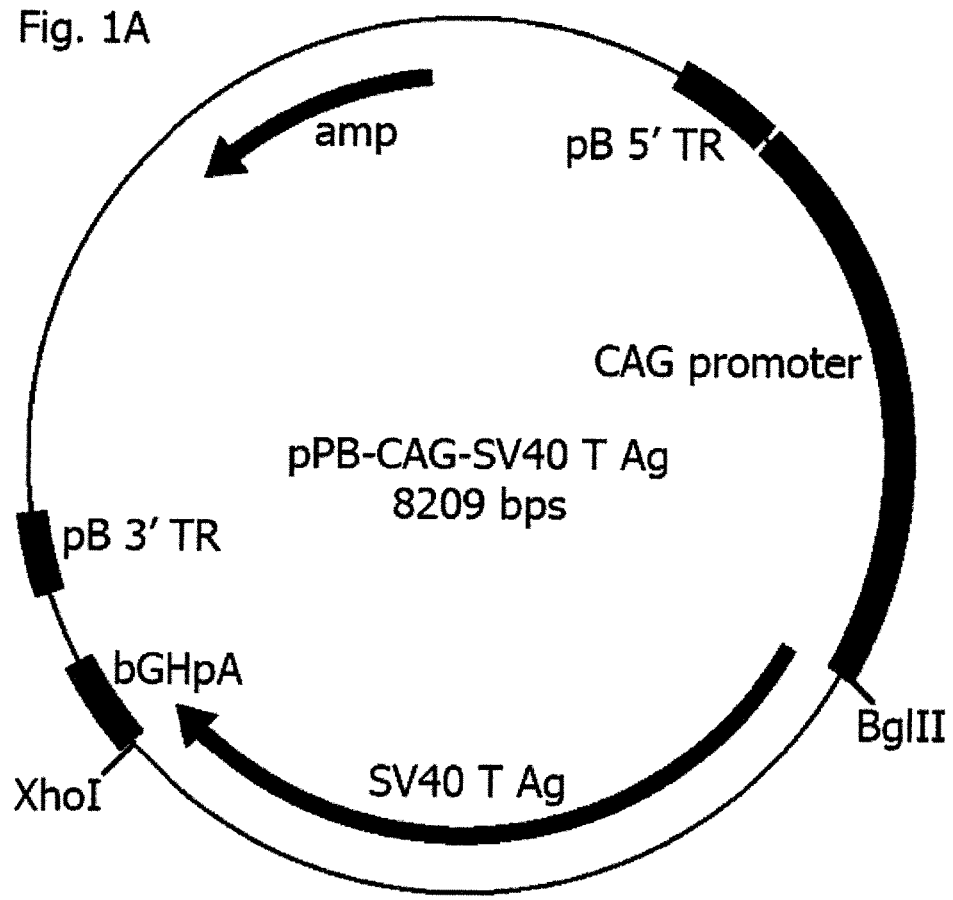

Specification includes a Sequence Listing.

(56) References Cited

OTHER PUBLICATIONS

Sherr, C.J. and Depinho, R.A., Cellular Senescence: Mitotic Clock or Culture Shock?, Cell, 2000, pp. 407-410, vol. 102.
Swanberg, S.E. and Delany, M.E., Dynamics of telomere erosion in transformed and non-transformed avian cells in vitro, Cytogenet Genome Res, 2003, pp. 318-325, 102.
Swanberg, S.E et al, Telomere biology of the chicken: A model for aging research, Experimental Gerontology, 2010, pp. 647-654, 45.
Venkatesan, R.N.,and Price, C., Telomerase expression in chickens: Constitutive activity in somatic tissues and town-regulation in culture, Proc. Natl. Acad. Sci. USA, Dec. 1998, pp. 14763-14768, vol. 95.
Ku, Y. et al., Effects of extopic expression of human telomerase reverse transcriptase on immortalization of feather keratinocyte stem cells, Journal of Experimental Zoology (Mol. Dev. Evol.), 2009, pp. 872-884, 312B.

\* cited by examiner

MERGAQPGVGVRRLRNVAREEPFAAVLGALRGCYAEATPLEAFVRRLQEGGTGEVEVLRG
DDAQCYRTFVSQCVVCVPRGARAIPRPICFQQLSSQSEVITRIVQRLCEKKKKNILAYGY
SLLDENSCHFRVLPSSCIYSYLSNTVTETIRISGLWEILLSRIGDDVMMYLLEHCALFML
VPPSNCYQVCGQPIYELISRNVGPSPGFVRRRYSRFKHNSLLDYVRKRLVFHRHYLSKSQ
WWKCRPRRGRVSSRRKRRSHRIQSLRSGYQPSAKVNFQAGRQISTVTARLEKQSCSSLC
LPARAPSLKRKRDGEQVEITAKRVKIMEKEIEEQACSIVPDVNQSSSQRHGTSWHVAPRA
VGLIKEHYISERSNSEMSGPSVVHRSHPGKRPVADKSSFPQGVQGNKRIKTGAEKRAESN
RRGIEMYINPIHKPNRRGIERRINPTHKPELNSVQTEPMEGASSGDRKQENPPAHLAKQL
PNTLSRSTVYFEKKFLLYSRSYQEYFPKSFILSRLQGCQAGGRRLIETIFLSQNPLKEQQ
NQSLPQQKWRKKRLPKRYWQMREIFQKLVKNHEKCPYLVFLRKNCPVLLSEACLKKTELT
LQAALPGEAKVHKHTEHGKESTEGTAPNSFLAPPSVLACGQPERGEQHPAEGSDPLLREL
LRQHSSHWQVYGFVRECLERVIPAELWGSSHNKCRFFKNVKAFISMGKYAKLSLQQLMWK
MRVNDCVWLRLAKGNHSVPAYEHCYREEILAKFLYWLMDSYVIELLKSFFYITETMFQKN
MLFYYRKFIWGKLQNIGIRDHFAKVHLRALSSEEMEVIRQKKYFPIASRLRFIPKMNGLR
PVVRLSRVVEGQKLSKESREKKIQRYNTQLKNLFSVLNYERTVNTSIIGSSVFGRDDIYR
KWKEFVTKVFESGGEMPHFYFVKGDVSRAFDTIPHKKLVEVISQVLKPESQTVYGIRWYA
VIMITPTGKARKLYKRHVSTFEDFIPDMKQFVSKLQERTSLRNAIVVEQCLTFNENSSTL
FTFFLQMLHNNILEIGHRYYIQCSGIPQGSILSTLLCSLCYGDMENKLLCGIQKDGVLIR
LIDDFLLVTPHLMQARTFLRTIAAGIPEYGFLINAKKTVVNFPVDDIPGCSKFKHLPDCR
LISWCGLLLDVQTLEVYCDYSSYAFTSIRSSLSFNSSRIAGKNMKCKLTAVLKLKCHPLL
LDLKINSLQTVLINIYKIFLLQAYRFHACVLQLPFNQKVRNNPDFFLRIISDTASCCYFI
LKAKNPGVSLGSKDASGMFPFEAAEWLCYHAFIVKLSNHKVIYKCLLKPLKVYKMHLFGK
IPRDTMELLKTVTEPSLCQDFKTILD*

IMMORTALISED CHICKEN EMBRYO FIBROBLASTS

CROSS-REFERENCE TO RELATED APPLICATIONS

This application is a national stage entry under 35 U.S.C. § 371 of PCT/EP2015/078457 filed on Dec. 3, 2015, which claims priority to EP Application No. 14196345.4 filed on Dec. 4, 2014. The content of PCT/EP2015/078457 is hereby incorporated by reference in its entirety.

The present invention relates to immortalised chicken embryo fibroblasts, to cell cultures comprising such immortalised cells, to vaccines comprising such cells, to methods for the replication of avian viruses on such cells, and to methods for the preparation of such cells and such vaccines.

The propagation of viruses for the purpose of vaccine production requires the availability of susceptible host cells. Usually, depending on the virus species and the type of host cell used, these host cells will be grown in cell culture. For the propagation of many avian virus species there is the additional possibility of propagation in embryonated eggs. However in practice, many avian virus species are grown on primary chicken embryo fibroblast (CEF) cells. (Cells that are cultured directly from an animal are known as primary cells). Such primary CEF cells are susceptible to many different virus species and such viruses can often be grown to high titers in these cells. Examples of viruses that are frequently grown on CEF cells are Herpes virus of turkey (HVT), Marek's virus, Newcastle Disease virus (NDV), Infectious Bronchitis virus (IBV), Infectious Bursal Disease virus (IBDV), Egg Drop Syndrome virus (EDSV), Reovirus (RV) and Turkey Rhinotracheitis virus (TRT).

However, there are several drawbacks to the use of CEF cells. They have a relatively short in vitro life span and they are obtained from embryonated specified pathogen-free eggs, so their production for continuous demand is both very laborious and very expensive. Thus it would be desirable to establish cell lines of avian origin to replace the use of primary CEF cells.

For the purpose of the present invention, an immortalized cell line is a population of cells (in this case CEFs) originating from a multicellular organism, which would normally not proliferate indefinitely but, due to mutation, has evaded normal cellular senescence and instead can keep undergoing cell division. Such cells have escaped the normal limitation of growth for only a finite number of division cycles.

An immortalised form of CEF cells (a CEF cell line) could in principle solve the problems identified above, but such cells are hardly available. One way of obtaining such cells is to isolate and grow primary CEF cells and to wait for a spontaneous immortalization event to happen. However, for avian cells, spontaneous immortalisation is very rare. As a consequence, only three spontaneously immortalised chicken cell lines have been reported; DF-1 (U.S. Pat. No. 5,672,485), SC-1 and SC-2 (Christman, S. A. et al., Dissertation Abstracts Int. 65: 4414 (2004) (ISBN 0-496-06882-2). Apart from the fact that finding and isolating a spontaneously immortalised CEF cell can be very time consuming, it also turns out that such immortalised CEF cells may show quite different characteristics such as variable growth rates and p53 levels over time, depending on the number of passages that they have had (Christman, S. A. et al., FEBS letters 579: 6705-6715 (2005)). However, especially for vaccine production purposes, cell lines are needed of which the characteristics remain the same over time, regardless the number of passages. The FDA has indicated that the development of minimally purified live attenuated viral vaccines in neoplastic cells that have been transformed by unknown mechanisms is discouraged (FDA; CBER Discussion on cell substrates May 12, 2000). Thus, spontaneously immortalised CEF cells are less desirable as a source of cells for virus propagation for vaccine purposes.

There are also methods known in the art for intentional immortalisation of cells. The advantage of such methods is that the coincidence factor, known to be a severe hindrance when aiming at spontaneously immortalised cells, is eliminated. For non-avian cells, especially mammalian cells, a frequently used method to obtain immortalised cells relies upon infection of primary cells with retroviruses or retroviral vectors, or transfection of primary cells with DNA molecules that comprise retroviruses or at least retroviral Long Terminal Repeat (LTR) sequences and sequences encoding DNA tumor virus oncoproteins such as Simian Virus SV40 T and t.

The SV40 T and t play a role in the inactivation of the retinoblastoma (Rb) and p53 proteins. A review paper by Deepika Ahuja et al., about SV40 T encoding large T and t provides insight in the mechanisms of action of these proteins (Oncogene 24: 7729-7745 (2005)). Basically, the SV40 T gene products T and t inhibit the p53 and Rb-family of tumor suppressors.

LTRs are retroviral elements that comprise all required signals for retroviral gene expression: enhancer, promoter, transcription initiation, transcription terminator and polyadenylation signal.

However, these LTRs are suspected of having tumorigenic effects. This is due to the fact that they are known to cis-activate other cellular genes and the fact that they may recombine with other retroviral sequences in the cellular genome (Mosier, D. E., Applied Biosafety 9: 68-75 (2004)). Thus, a severe disadvantage of the use of retroviral DNA comprising LTRs or at least long retroviral sequences for transfecting cells is that in such cases LTR sequences will be introduced into the DNA of the immortalised cells.

For avian cells, only one example of a successful immortalisation with a DNA molecule comprising LTRs and expressing SV40 T antigen is known: such immortalised CEF cells are described in PCT Application WO 97/44443.

Such methods are apparently not very successful. Soo-Hyun Kim described transfection of CEF cells with a retrovirus encoding SV40 T antigen, in an attempt to immortalise CEF cells through inactivation of the retinoblastoma (Rb) and p53 tumor suppressors. (J. Cell Science 119: 2435-2443 (2006)). This however only led to a slight extension of the life span of the CEF cells, not to immortalisation.

Kim at that time suggested that a possible explanation for the limited lifespan extension could be the continued erosion of telomeres. However, the situation is complicated by the fact that chicken cells contain both macro- and micro-chromosomes with different size classes of telomeric repeats, some of which are interstitial. Thus, at this juncture the dynamics of telomere erosion and repair and their effect on immortalisation of chicken cells remain unclear.

This touches upon the basic and unsolved question if a critical role in immortalisation of CEF relates to the loss of p53 and Rb or the activation of telomerase (Campisi, J., Exp. Gerontol. 36: 607-618 (2001) and Sherr, J. C. and DePinho, R. A., Cell 102: 407-410 (2000)).

It can be derived from recent experiments that, contrary to Kim's suggestion, the role of telomerase in the immortalisation of CEF cells appears not to be a critical one. First of all, it is striking that in the spontaneously immortalised CEF cell line SC-1 (see above) no telomerase expression is detectable (Christman, S. A. et al., FEBS letters 579: 6705-6715 (2005)).

Secondly, in several straightforward experiments in which chicken cells were transduced or transfected with cTR, cTERT or both cTR and cTERT, no immortalised chicken cells were obtained (Swanberg, S. E. et al., Exp. Gerontol. 45: 647-654 (2010)).

It has now contrary to all expectations been found that stably transfected CEF cell lines can be obtained through transfection of CEF cells, without the use of LTR sequences, with a DNA molecule comprising transposon inverted repeats for the integration of the DNA molecule into the cellular genome and a combination of both the gene encoding the SV40 T and t antigen or at least T under the control of a suitable promoter, and the gene encoding chicken telomerase (cTERT) under the control of a suitable promoter. The transposon inverted repeats play a role in the stable integration of the gene encoding the SV40 T and t antigen or at least T and the gene encoding (cTERT) into the genome of the CEF, which is a prerequisite for obtaining a stably transfected immortalised CEF according to the invention.

Thus, a first embodiment of the present invention relates to a stably transfected immortalised chicken embryo fibroblast (CEF), characterized in that the stably transfected immortalised CEF expresses an SV40 T antigen, expresses chicken telomerase (cTERT) and does not comprise exogenous retroviral Long Terminal Repeat DNA.

Exogenous retroviral LTR DNA is considered to be DNA that is brought into a chicken embryo fibroblast during the process of immortalisation as described above.

The details and characteristics of such immortalised CEF as well as methods for the preparation of such CEF are extensively described below.

A second embodiment of the present invention relates to methods for the preparation of such immortalised CEF cell lines.

Methods for the preparation of an immortalised CEF cell line according to the invention basically comprise the following steps:
a) the step of obtaining primary CEF cells. This step is well-known in the art and has been described i.a. by Hernandez, R and Brown, D. T. in Current protocols in Microbiology 17: A.4i.1-A.4i.8 (2010) and by others. It still is the preferred way of obtaining CEFs.
b) the step of transfecting said CEFs with 1) a DNA molecule free of LTR sequences, comprising transposon inverted repeats and comprising a gene encoding the SV40 T antigen under the control of a suitable promoter, 2) a DNA molecule free of LTR sequences, comprising transposon inverted repeats and comprising a gene encoding chicken telomerase; cTERT under the control of a suitable promoter and 3) a DNA molecule comprising a gene encoding transposase under the control of a suitable promoter.

The DNA molecule comprising a gene encoding transposase under the control of a suitable promoter needs not necessarily to be free of LTR sequences, because this DNA molecule itself does not comprise transposon sequences and will thus not likely be integrated in the host's genome. Nevertheless, in order to avoid unintended accidental integration, preferably the DNA molecule comprising a gene encoding transposase under the control of a suitable promoter is free of LTR sequences.

For reasons of efficiency, in practice the transfection would preferably be done with a single DNA molecule free of LTR sequences, comprising transposon inverted repeats, comprising both a gene encoding the SV40 T antigen under the control of a suitable promoter and a gene encoding chicken telomerase under the control of a suitable promoter and comprising a gene encoding transposase under the control of a suitable promoter.

The transposase activity is necessary only during the first steps of the immortalisation process for integration of the DNA in the CEF genome. Once the DNA(s) is/are integrated, the transposase is no longer needed. Afterwards it may even become detrimental to the stability of the cells.

Thus, even more preferably the step of transfecting said CEFs would be done with 1) a single DNA molecule free of LTR sequences, comprising transposon inverted repeats and comprising both a gene encoding the SV40 T antigen under the control of a suitable promoter and a gene encoding chicken telomerase under the control of a suitable promoter and 2) a DNA molecule, preferably free of LTR sequences, only comprising the transposase-gene under the control of a suitable promoter without transposon sequences.

Transfection can be done in many ways known in the art. Commercial kits for transfection are currently available through i.a. Bio-Rad (Life Science (Research, Education, Process Separations, Food Science), Life Science Research, 2000 Alfred Nobel Drive, Hercules, Calif. 94547, USA) and Invitrogen (Life Technology, 3175 Staley Road, Grand Island, N.Y. 14072, USA). Commonly used reagent-based transfection methods comprise the use of lipids, calcium phosphate, cationic polymers, DEAE-dextran, activated dendrimers and magnetic beads. Instrument-based methods comprise electroporation, nucleofection and micro-injection.

A DNA molecule free of LTR sequences, comprising transposon inverted repeats, comprising a gene encoding the SV40 T antigen under the control of a suitable promoter and transposon inverted repeats and/or the gene encoding chicken telomerase under the control of a suitable promoter could e.g. be a plasmid. The plasmid may be in a circular or linear form when it is used for the transfection step.

The use of transposons as such is well-known in the art. A paper by Ivics, Z. and Izsvak Z. extensively reviews transposons and their use, and provides insight in the mechanisms of action of transposons (Mobile DNA 1: 25-39 (2010)). Transposons can be viewed as natural DNA transfer vehicles that, similar to integrating viruses, are capable of efficient genomic insertion, mediated by transposase.

In principle, the transposons remain stably present in the cellular genome after integration in the genome. Therefore, preferably immortalized CEFs according to the invention comprise transposon sequences such as the transposon inverted repeats.

A large number of suitable promoters for the expression of the SV40 T antigen and the cTERT are known in the art, which are recognized for their efficient level of expression. It is known that promoters which are transcriptionally active in mammalian cells also function well in avian cells. Such promoters include classic promoters such as the (human) cytomegalovirus immediate early promoter (Sun-Young Lee et al., Journal of Biomedical Science 6: 8-17 (1999), Seed, B. et al., Nature 329, 840-842, 1987; Fynan, E. F. et al., PNAS 90, 11478-11482, 1993; Ulmer, J. B. et al., Science 259, 1745-1748, 1993), the Human Cytomegalovirus enhancer-promoter (Donofrio G., et al., Clinical and Vaccine Immunology 13: 1246-1254, (2006)), the Mouse Cytomegalovirus immediate early (MCMViel) promoter, the Mouse Cytomegalovirus early (MCMVe1) promoter, SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992).

A preferred promoter is the CAG promoter. (Miyazaki, J; Takaki, S; Araki, K; Tashiro, F; Tominaga, A; Takatsu, K; Yamamura, K., Gene 79 (2): 269-277 (1989), and Niwa, H; Yamamura, K; Miyazaki, J., Gene 108 (2): 193-199 (1991)).

c) the step of selecting cells that are capable of sustained proliferation.

CEF cells that are capable of sustained proliferation are cells that keep proliferating for at least 45 population doublings. The cell cycle, or cell-division cycle, is the series of events that take place in a cell leading to its division and duplication (the cell replication). The selection of cells that are capable of sustained proliferation is a very simple process for the following reason: primary CEFs are, even in the most optimal situation, not capable of dividing outside their natural environment, the avian embryo, for more than 45 times. After an initial phase of proliferation, the proliferation rate of live primary CEF cells after isolation decreases over time and eventually all primary CEF cells enter into a non-proliferative stage. As a consequence they will die off after a maximum of about 45 population doublings.

This means that if there is an increase in the number of cells, especially after 45 population doublings, this must be due to the fact that one or more cells have successfully been transfected and that the gene encoding the SV40 T antigen and the gene encoding cTERT are inserted in the cellular genome. So basically the process is self-selecting: maintenance of CEFs some of which were successfully transfected, in a suitable cell growth medium will automatically lead to replication of these transfected cells, whereas non-immortalised cells will stop dividing and die off. Suitable cell growth media are known in the art (see Kim, 2006 and Hernandez, 2010 above) and are described i.a. in the Examples section.

Further guidance about cell culture conditions can be found in the Examples.

Usually, cells are selected that have been cultured for at least 45 cell cycles. For such cells it can reasonably be assumed that they are successfully immortalized CEFs, since primary CEFs will usually not replicate more than about 45 times in vitro after isolation from the chicken embryo.

Thus, one embodiment of the present invention relates to a method for the preparation of an immortalised CEF according to the invention, wherein that said method comprises the steps of
  a) obtaining primary CEF cells,
  b) transfecting said CEFs with 1) a DNA molecule free of LTR sequences, comprising transposon inverted repeats and comprising a gene encoding the SV40 T antigen under the control of a suitable promoter, 2) a DNA molecule free of LTR sequences, comprising transposon inverted repeats and comprising a gene encoding chicken telomerase; cTERT under the control of a suitable promoter and 3) a DNA molecule free of LTR sequences, comprising a gene encoding transposase under the control of a suitable promoter.
  c) selecting CEF cells that have been cultured for at least 45 cell cycles.

A preferred form of this embodiment relates to a method for the preparation of an immortalised CEF according to the invention, characterized in that said method comprises the steps of
  a) obtaining primary CEF cells,
  b) transfecting said primary CEF cells with a single DNA molecule free of LTR sequences, comprising transposon inverted repeats, comprising both a gene encoding the SV40 T antigen under the control of a suitable promoter and a gene encoding chicken telomerase under the control of a suitable promoter and comprising a gene encoding transposase under the control of a suitable promoter,
  c) selecting CEF cells that have been cultured for at least 45 cell cycles.

A more preferred form of this embodiment relates to a method for the preparation of an immortalised CEF according to the invention, characterized in that said method comprises the steps of
  a) obtaining primary CEF cells,
  b) transfecting said primary CEF cells with 1) a DNA molecule free of LTR sequences, comprising transposon inverted repeats, comprising both a gene encoding the SV40 T antigen under the control of a suitable promoter and a gene encoding chicken telomerase under the control of a suitable promoter and with 2) a DNA molecule free of LTR sequences, comprising a gene encoding transposase under the control of a suitable promoter,
  c) selecting CEF cells that have been cultured for at least 45 cell cycles.

In exceptional cases, cells that went through around 45 cell cycles may still show instable behavior, e.g. due to the fact that the transposon has integrated in the cellular genome at a very critical site, or due to instable integration of the gene encoding the SV40 T antigen or encoding cTERT. Therefore, in practice preferably cells are selected that have been cultured for at least 50, 60, 70, 80, 90, 100, 110, 120, 130, 140, 150 or even 160 cell cycles, in that order of preference. The chances of any instability becoming manifest do decrease with the amount of cell cycles of the selected immortalised CEF.

Thus, preferably, cells are selected that have been cultured for at least 50, 60, 70, 80, 90, 100, 110, 120, 130, 140, 150 or even 160 cell cycles, in that order of preference.

A third embodiment of the present invention relates to methods for the replication of an avian virus or an avian viral vector, said methods comprising the steps of
  a) culturing an immortalised CEF according to the invention,
  b) contacting the immortalised CEF with the avian virus or avian viral vector
  c) allowing the avian virus or avian viral vector to replicate and
  d) isolating the progeny virus.

Avian viruses of special interest are the following avian viruses: Herpes virus of turkey (HVT), Marek's virus, Newcastle Disease virus (NDV), Infectious Bronchitis virus (IBV), Infectious Bursal Disease virus (IBDV), Egg Drop Syndrome virus (EDSV), Reovirus (RV) and Turkey Rhinotracheitis virus (TRT). For all these viruses, vaccines are known in the art, either on the basis of live attenuated viruses, inactivated viruses or recombinant viruses; viral vectors, expressing immunogenic components of any of these viruses.

A viral vector is a virus that carries an additional gene, not present in the wild-type form of the virus. Viral vectors are very well-known in the art. Viral vectors can be used to carry e.g. a foreign bacterial gene or a foreign viral gene. Usually, the additional gene is placed under the control of a suitable promoter. Examples of such viral vectors are e.g. a HVT vector comprising the IBDV VP2-gene, the IBV-spike protein gene, the avian influenza HA gene, the ILT gD/gI protein gene or the NDV F-gene.

Thus, a preferred form of this embodiment relates to methods of replicating an avian virus or an avian viral vector, according to the invention, wherein the avian virus or the avian viral vector is selected from the group of avian viruses consisting of Marek's Disease virus (MDV), the MDV-related Herpes virus of turkey (HVT), Newcastle Disease virus (NDV), Infectious Bronchitis virus (IBV), Infectious Bursal Disease virus (IBDV), Egg Drop Syndrome virus (EDSV), Reovirus (RV), Turkey Rhinotracheitis virus (TRT) and a HVT vector comprising the IBDV VP2-gene, the IBV-spike protein gene, the avian influenza HA gene, the ILT gD/gI protein gene or the NDV F-gene.

Marek's Disease virus (MDV) is a herpesvirus known to exist in three serotypes: the highly virulent serotype 1, the moderately virulent serotype 2 and the serotype 3, a turkey virus that is not virulent to chickens; the Marek-related virus Herpes virus of turkey (HVT).

The immortalised CEF cells according to the invention are very suitable for the propagation of the three MDV-serotypes.

Thus, a more preferred form of this embodiment relates to methods for the replication of an avian virus according to the invention wherein the avian virus is selected from the group of avian viruses consisting of MDV and MDV vector virus.

A fourth embodiment of the present invention relates to a cell culture comprising an immortalised CEF according to the invention.

A preferred form of this embodiment relates to such a cell culture that is infected with an avian virus or an avian viral vector.

A more preferred form of this embodiment relates to such a cell culture that is infected with an avian virus or an avian viral vector selected from the group consisting of Marek's Disease virus (MDV), the MDV-related Herpes virus of turkey (HVT), Newcastle Disease virus (NDV), Infectious Bronchitis virus (IBV), Infectious Bursal Disease virus (IBDV), Egg Drop Syndrome virus (EDSV), Turkey Rhinotracheitis virus (TRT), Reovirus (RV) and a HVT vector comprising the IBDV VP2-gene, the IBV-spike protein gene, the avian influenza HA gene, the ILT gD/gI protein gene or the NDV F-gene.

An even more preferred form of this embodiment relates to such a cell culture wherein the cell culture is infected with MDV or an MDV virus vector.

A fifth embodiment of the present invention relates to methods for the preparation of a vaccine comprising an avian virus or an avian viral vector wherein that method comprises the step of mixing a cell culture according to the invention wherein the cell culture is infected with an avian virus or an avian viral vector, with a pharmaceutically acceptable carrier.

In a preferred form of this embodiment the avian virus or an avian viral vector is selected from the group consisting of Marek's Disease virus (MDV), the MDV-related Herpes virus of turkey (HVT), Newcastle Disease virus (NDV), Infectious Bronchitis virus (IBV), Infectious Bursal Disease virus (IBDV), Egg Drop Syndrome virus (EDSV), Reovirus (RV), Turkey Rhinotracheitis virus (TRT) and a HVT vector comprising the IBDV VP2-gene and/or the NDV F-gene.

Some MDV-related viruses are only capable of surviving if they are bound to the cell in which they are grown. Serotype 1 is capable of surviving without being bound to a cell. Serotype 2 is less likely to survive without being bound to a cell. Serotype 3 (HVT) does not survive when separated from the cell in which it is grown Immortalised CEFs according to the invention are very suitable to grow these MDV serotypes. So for MDV, especially for MDV serotypes 2 and 3 it goes that immortalised CEFs according to the invention that are infected with these MDV serotypes are very suitable for use in a vaccine comprising cell-bound MDV. Such vaccines can be made according to standard techniques known in the art for the preparation of cell-bound MDV vaccines, by mixing such MDV-infected immortalised CEFs and a pharmaceutically acceptable carrier.

Thus, in a more preferred form of this embodiment the avian virus or avian viral vector is MDV.

In an even more preferred form of this embodiment, the MDV or MDV viral vector is in a live attenuated form.

A sixth embodiment of the present invention relates to methods for the preparation of a vaccine comprising an avian virus or an avian viral vector, wherein the method comprises the steps of
a) infecting a cell culture of CEF according to the invention with an avian virus or an avian viral vector
b) replicating said avian virus or an avian viral vector
c) isolating the progeny virus
d) mixing the progeny virus with a pharmaceutically acceptable carrier A preferred form of this embodiment relates to such a vaccine wherein the avian virus or an avian viral vector is selected from the group consisting of Marek's Disease virus (MDV), the MDV-related Herpes virus of turkey (HVT), Newcastle Disease virus (NDV), Infectious Bronchitis virus (IBV), Infectious Bursal Disease virus (IBDV), Egg Drop Syndrome virus (EDSV), Reovirus (RV), Turkey Rhinotracheitis virus (TRT) and a HVT vector comprising the IBDV VP2-gene and/or the NDV F-gene.

A more preferred form of this embodiment relates to such a vaccine wherein the avian virus or an avian viral vector is MDV or an MDV vector.

As says above, some MDV-related viruses are only capable of surviving if they are bound to the cell in which they are grown. So for MDV, especially for MDV serotypes 2 and 3 it goes that immortalised CEFs according to the invention that are infected with these MDV serotypes are very suitable for use in a vaccine comprising cell-bound MDV. Such vaccines can be made according to standard techniques known in the art for the preparation of cell-bound MDV vaccines, by mixing such MDV-infected immortalised CEFs and a pharmaceutically acceptable carrier.

Thus, a seventh embodiment of the present invention relates to vaccines comprising an immortalised CEF cell culture according to the invention wherein that cell culture is infected with an MDV, and a pharmaceutically acceptable carrier.

LEGEND TO THE FIGURES

FIG. 1: Vector maps for pPB-CAG-SV40 T Ag (A) and pPB-CAG-cTERT (B).

FIG. 2: cTERT amino acid sequence. * indicates stop codon.

Figure 3:
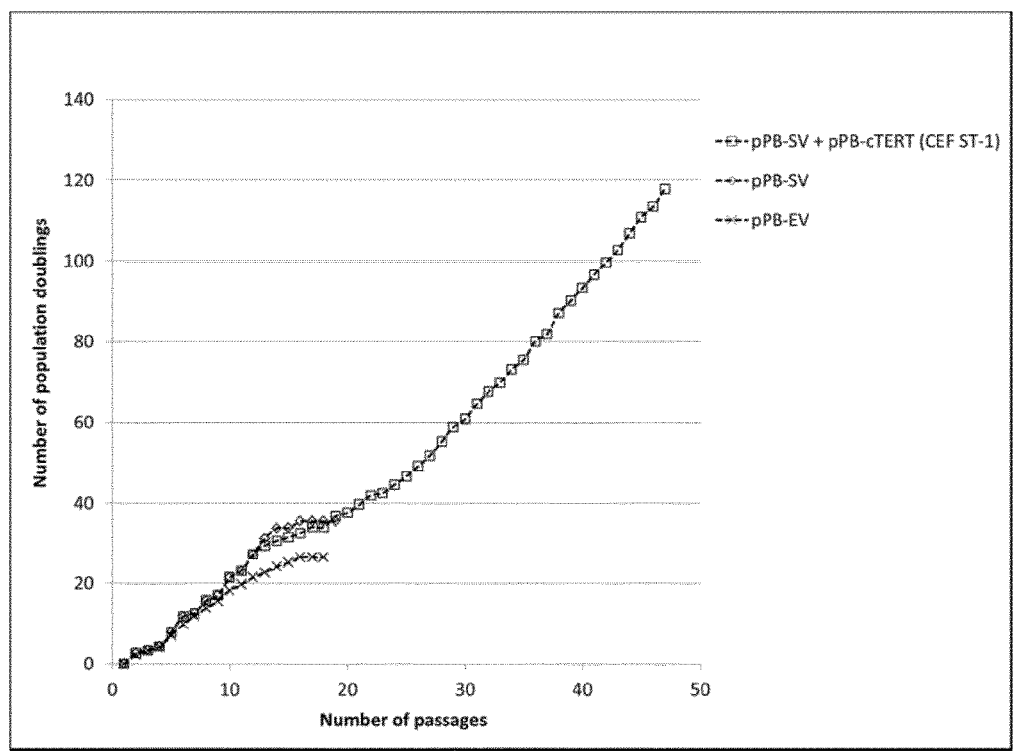

FIG. 3: Growth curve of the CEF ST-1 cell line. Cells transfected with pPB-EV (crosses), pPB-SV (diamonds) or pPB-SV and pPB-cTERT (CEF ST-1) (squares) were passaged. Cell numbers were determined at each passage to calculate the population doublings per passage.

Figure 4:
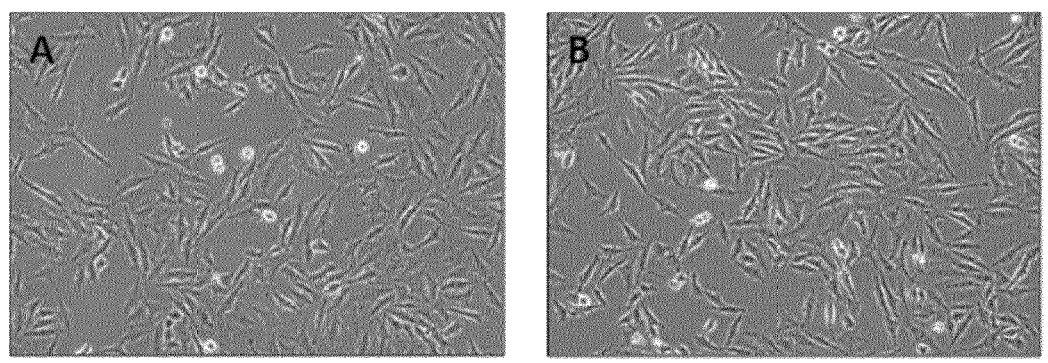

FIG. 4: CEF ST-1 morphology remains constant during passaging. CEF ST-1 cells were photographed at passage 25 (100×)(A) and passage 44 (100×)(B).

Figure 5:
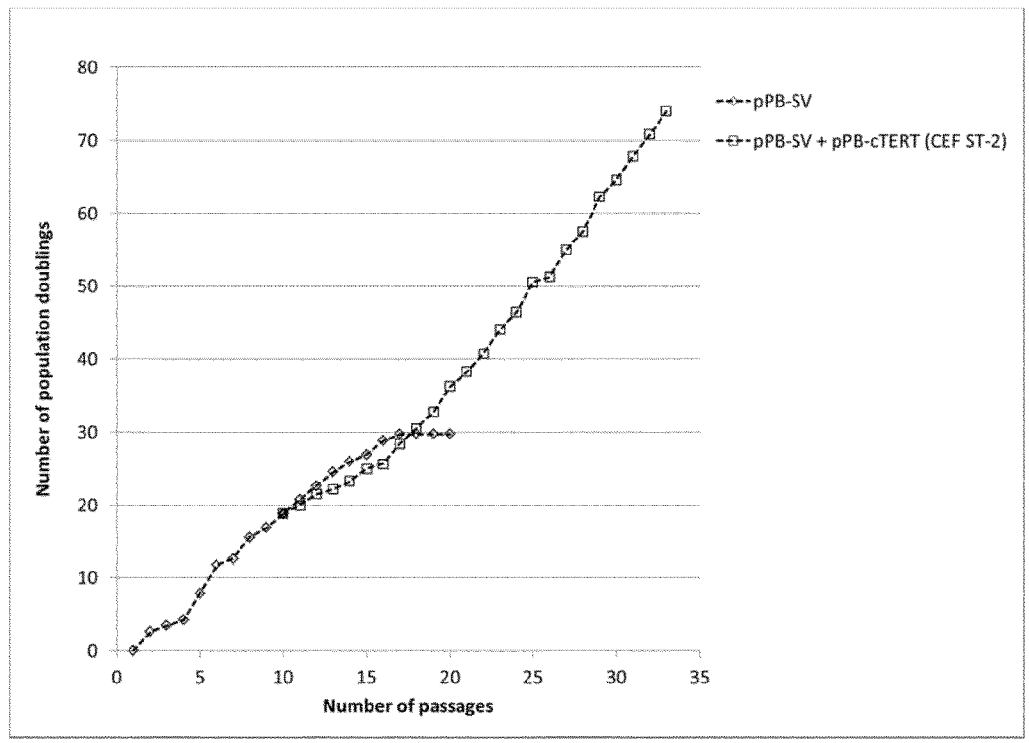

FIG. 5: Growth curve of the CEF ST-2 cell line. Cells transfected with pPB-SV (diamonds) or pPB-SV and pPB-cTERT (CEF ST-2) (squares) were passaged. Cell numbers were determined at each passage to calculate the population doublings per passage.

Figure 6:
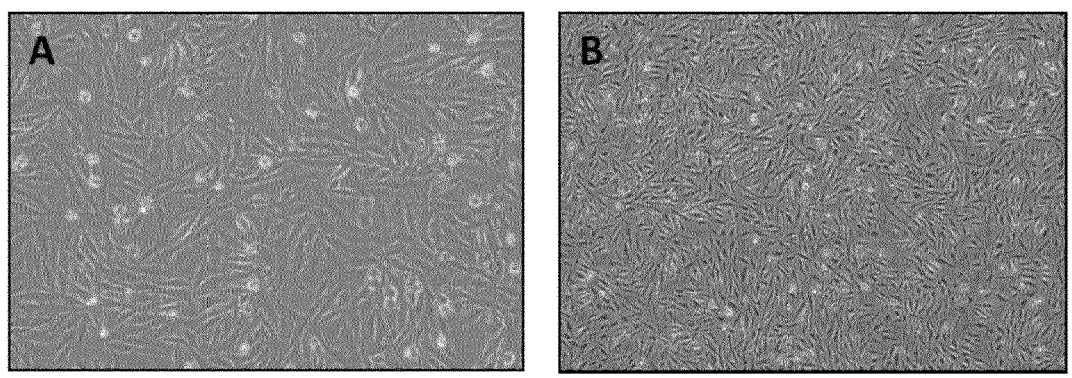

FIG. 6: CEF ST-2 morphology remains constant during passaging. CEF ST-2 cells were photographed at passage 19 (100×)(A) and passage 26 (40×)(B).

Figures 7, 8, 9:
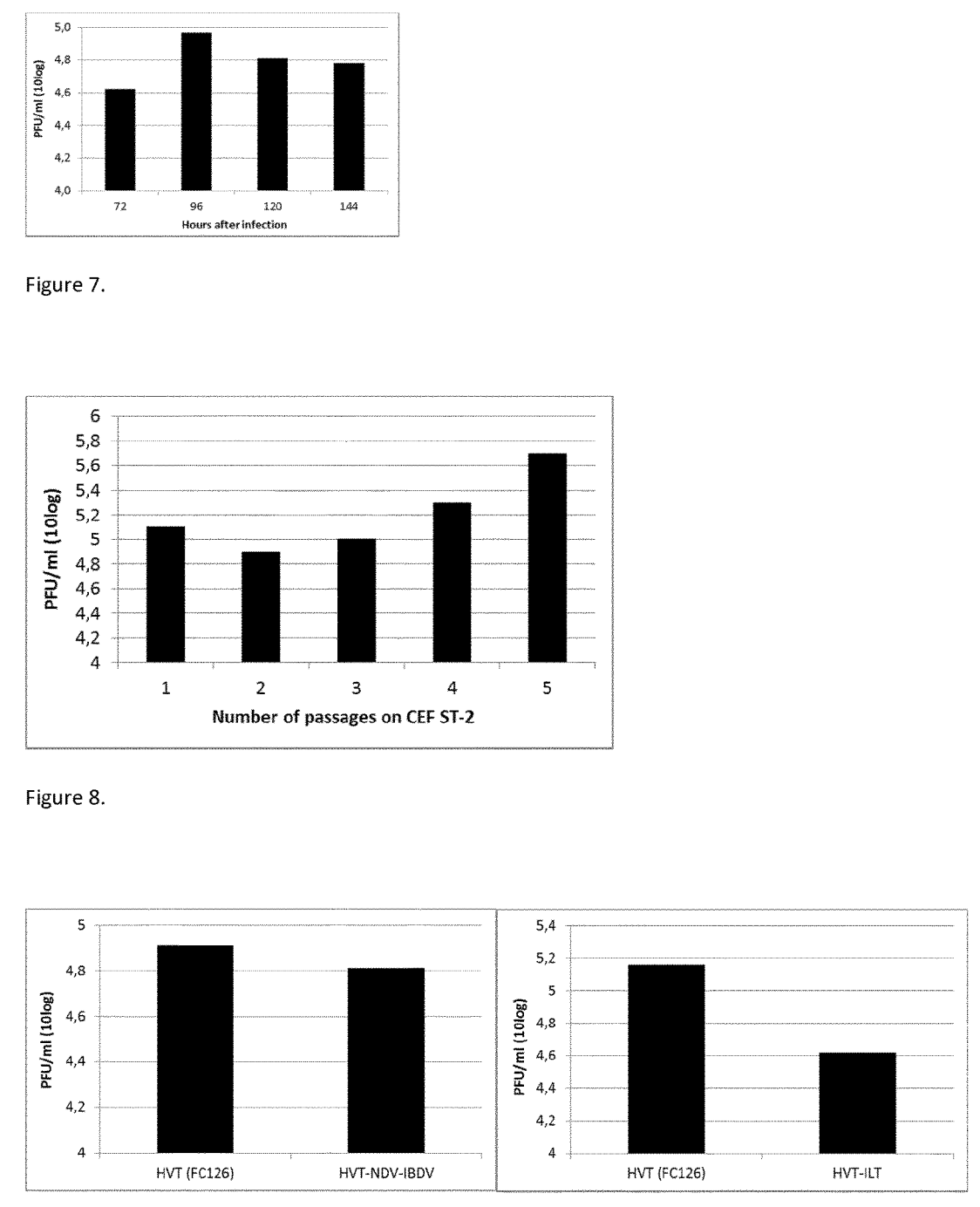

FIG. 7: HVT replication in CEF ST-2 cells. CEF ST-2 cells were infected with HVT at T=0 with an MOI of 0.05. Cells were harvested at the indicated time-points and HVT titers were determined by titration.

FIG. 8: CEF ST-2 cells were infected with HVT at T=0 with an MOI of 0.05. Cells were trypsinized and harvested after 96 hours and reseeded on a fresh CEF ST-2 monolayer. This procedure was repeated 4 times. At each passage, samples were harvested to determine the HVT titer.

FIG. 9: CEF ST-2 cells were infected with HVT or recombinant HVT viruses at T=0 with an MOI of 0.05. Cells were trypsinized and harvested after 96 hours. HVT titers were determined by titration.

EXAMPLES

Example 1: Immortalization of Chick Embryonic Fibroblasts

Plasmids.

To construct pPB-CAG-SV40 T Ag, XhoI and BglII sites were added to SV40 T Ag by PCR using primers SV40 Tag 5'-BII (5'-GGCGAGATCTACCATGGATAAAGTTT-TAAACAG-3') and SV40 Tag 3'-XI (5'-GGCGCTCGAGT-TATGTTTCAGGTTCAGGGG-3'). Phusion DNA polymerase was used for PCR according to the manufacturer's protocol (New England Biolabs). The fragment was cloned into pCR-Blunt (Life Technologies) and verified by sequencing. Next, SV40 T Ag was excised from pCR-Blunt and cloned into pPB-CAG-EBNXN (Yusa et al., 2009) using the BglII-XhoI sites to create pPB-CAG-SV40 T Ag (FIG. 1A). The final construct was verified by sequencing.

Figure 1B:
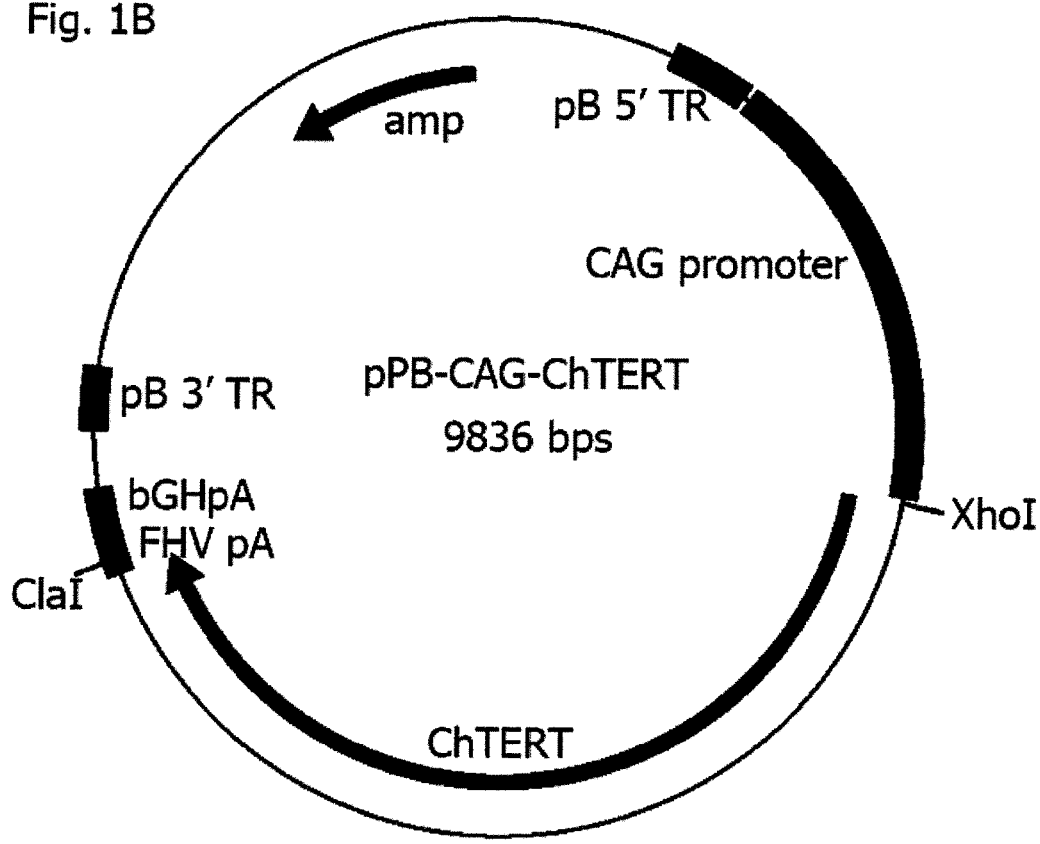

The sequence encoding cTERT followed by a feline herpesvirus polyA signal sequence (CAATAAACATAG-CATACGTTATGACATGGTCTACCGCGTCT-TATATGGGGACGAC) (Willemse et al., 1995) was generated synthetically, sequenced and cloned into pPB-CAG-EBNXN (Yusa et al., 2009) using the XhoI-ClaI sites to create pPB-CAG-cTERT (FIG. 1B and FIG. 2). Plasmid DNA for transfection into CEFs was isolated using the Qiagen EndoFree plasmid maxi kit (Qiagen).

Isolation and Growth of CEFs.

Ten SPF eggs were incubated at 37° C. for ten days and used for isolation of primary embryonic fibroblasts. Embryos were harvested from the eggs under sterile conditions. After removal of the head, legs and wings, embryos were washed three times in sterile PBS and dissociated using a trypsin/EDTA solution. After dissociation, fetal calf serum was added to inactivate trypsin. The isolated cells were centrifuged for 15 minutes at 400×g. Pelleted cells were resuspended in DMEM containing 5% fetal calf serum (Moregate), 1% chicken serum (Sigma), 2 mM glutamine, 1 mM sodium pyruvate and antibiotics, stained for viability and counted. $2 \cdot 10^5$ cells/cm2 were plated in culture flasks and incubated at 40° C. and 5% $CO_2$.

Transfection

After 3 days in culture, CEFs were harvested and viable cells were counted before transfection. Per transfection, $1 \cdot 10^6$ viable cells were transfected in 100 μl Primary cell buffer P3+supplement (Lonza Cologne AG) using program CA-137 of the Nucleofector 4D device (Lonza Cologne AG). Cells were transfected with 1,6 μg pPB-CAG-SV40 T Ag and 0,4 μg pPB-CMV-hyPBase (Yusa et al., 2011) or, as a control, with 1,6 μg pPB-CAG-EBNXN and 0,4 μg pPB-CMV-hyPBase. After administration of the pulse, cells were left at RT for 5 min. Next, 400 μl RPMI 1640 (37° C.) was slowly added to the cells and cells were incubated at 37° C. for 5 minutes. Then, cells were carefully resuspended, seeded in T25 flasks in growth medium and incubated at 40° C. and 5% $CO_2$. Transfection of the CEF+pPB-CAG-SV40 T Ag cells with pPB-CAG-cTERT was performed using the same protocol. Here, CEFs stably transfected with pPB-CAG-SV40 T Ag were transfected with 1,6 μg pPB-CAG-cTERT and 0,4 μg pPB-CMV-hyPBase (Yusa et al., 2011) or, as a control, either with 1,6 μg pPB-CAG-EBNXN and 0,4 μg pPB-CMV-hyPBase or with 2 μg of a standard GFP expression vector (pmaxGFP, Lonza).

Tissue Culture

After transfection, cultures were grown in growth medium (DMEM containing 5% fetal calf serum (Moregate), 1% chicken serum (Sigma), 2 mM glutamine, 1 mM sodium pyruvate) and routinely passaged upon 80-90% confluency. After removal of the medium, cells were washed twice with PBS and trypsinized using a trypsin/EDTA solution. Cells were resuspended in growth medium and pelleted. The pelleted cells were resuspended in growth medium and counted using a Bürker-Türk counting chamber. Cells were plated in fresh medium in Cellbind tissue culture flasks (Corning) and incubated at incubated at 40° C. and 5% $CO_2$. CEF+pPB-CAG-SV40 cells were frozen for liquid nitrogen storage at different passages in standard medium containing 42.5% FCS and 10% DMSO. CEF+pPB-CAG-SV40 T Ag cells transfected with p-PB-CAG-cTERT or with control plasmids were plated on collagen I-coated surfaces (Biocoat, Corning) in normal growth medium or animal component free medium+1% newborn calf serum (Hyclone, ThermoFisher). The number of population doublings was calculated using the following equation:

$$\text{Population doublings} = \frac{\log Nt - \log N}{\log 2},$$

where Nt was the number of viable cells at the end of the growth period and N the number of plated cells (Venkatesan and Price, 1998). Cells were photographed using an Olympus DP21 camera coupled to an Olympus CKX41 microscope.

Infection

Cells were seeded 24 hours prior to infection at a density of $1 \cdot 10^5$ cells/cm2 in animal component free medium with or without 0.25% newborn calf serum and incubated at 40° C. and 5% CO2. Cells were infected with an MOI of 0.05 plaque forming units (PFU). Viruses used were HVT (FC126), a recombinant HVT expressing both an NDV F and an IBDV VP2 antigen (HVT-NDV-IBDV) and a recombinant HVT expressing an ILT gD/gI antigen (HVT-ILT). After infection, cells were incubated at 38.5° C. and 5%

CO$_2$. Medium was replenished completely after 72 hours in case cells were incubated for more than 72 hours. Depending on the experiment, samples for titration were harvested 72, 96, 120 or 144 hours after infection and frozen for liquid nitrogen storage: After removal of the medium, cells were washed twice with PBS and trypsinized using a trypsin/EDTA solution. Cells were resuspended in growth medium and pelleted. After removal of the supernatant, cells were resuspended in fresh growth medium and counted. Next, 1·10^7/ml cells were frozen in growth medium containing a final concentration of 10% DMSO and 20% fetal calf serum and stored in liquid nitrogen.

Titration

Ampoules of the frozen HVT-infected cells were thawed and the number of PFU/ml was determined by titrating the HVT-infected cells on CEFs. Plaques were visualized with an immunofluorescence assay using monoclonal antibodies or polyclonal chicken serum recognizing HVT. Goat-anti-chicken Alexa 488 antibodies or goat-anti-mouse Alexa 488 antibodies were used as secondary antibodies, respectively. All titrations were performed in duplo.

Results

Expression of SV40 T Antigen Extends the Lifespan of Primary CEFs.

Primary CEFs were transfected at passage 1 with pPB-CAG-SV40 T Ag (pPB-SV) and a piggyBac transposase expression vector to obtain genomic integration and stable expression of SV40 T Ag. As a control, CEFs were also transfected with the empty pPB-CAG-EBNXN (pPB-EV) vector. After transfection, cells were routinely passaged at 80-90% confluency and counted to determine the number of viable cells. The number of viable cells at passaging was used to calculate the number of doublings of the population after seeding (population doublings (PDs)). Although SV40 T Ag expressing cells showed an extended lifespan compared to controls (35 population doublings versus 26 population doublings, respectively), all cultures eventually stopped growing around passage 17 (FIG. 3). After passage 17, proliferating cells were still present in the cultures. However, since many cells in the culture died, no increase in total cell numbers was found and eventually all cells died.

CEF+pPB-SV cells were examined for SV40 T Ag expression at different passages with an immunofluorescence assay using a monoclonal antibody specific for SV40 T Ag. At passage 2, one passage after transfection, a small number of cells was SV40 T Ag positive. Nearly all cells expressed SV40 T Ag after passage 7 (data not shown).

Expression of cTERT in SV40 T Ag-Expressing Cells Induces Immortalization.

CEF ST-1 Cell Line

To obtain immortalized CEFs we transfected CEF+pPB-SV cells with the pPB-CAG-cTERT (pPB-cTERT) expression vector. CEF+pPB-SV passage 13 ampoules were thawed, cells were taken into culture, passaged and transfected at passage 18 with pPB-cTERT and the transposase expression vector. The total number of CEF+pPB-SV cells at passage 18 was low. Therefore we used the CEF+pPB-SV cells that were transfected with a standard GFP expression vector (EV) to determine transfection efficiency also as empty vector controls during passaging. After transfection, cells were seeded and examined daily for proliferation and outgrowth of colonies. No proliferation was observed in the CEF+pPB-SV+EV cultures and all cells eventually died (data not shown). In the CEF+pPB-SV+pPB-cTERT cultures, however, rapidly proliferating colonies were clearly visible after 10 days. These colonies were trypsinized, cells were counted and seeded in tissue culture flasks. We found that these cells proliferated better in animal component free (ACF) medium than in our standard growth medium (data not shown), therefore we continued to grow these cells in ACF medium. These CEF+pPB-SV+pPB-cTERT cells continued to grow vigorously and were passaged until they had performed over 100 population doublings (PDs) (FIG. 3).

At this point, cells were still healthy and proliferating vigorously. Therefore, we concluded that we had established an immortalized CEF cell line and named it CEF ST-1 (for CEF+SV40 T Ag+cTERT-nr.1). The cells have a fibroblastic morphology which remains constant during passaging (FIG. 4).

CEF ST-1 cells of different passages have been frozen down in ampoules for liquid nitrogen storage. These cells can be easily regrown after liquid nitrogen storage.

CEF ST-2 Cell Line

CEF ST-1 was generated by transfecting passage 18 CEF+pPB-SV cells with the cTERT expression vector. At this point, a limited number of cells was still proliferating and many cells in the culture had already died. Since only a small number of immortalized colonies grew out after cTERT transfection and gave rise to the CEF ST-1 cell line, we conclude that CEF ST-1 is an oligoclonal cell line.

In order to establish a polyclonal cell line, i.e. a cell line originating from many different immortalized CEF cells, we also transfected early passage CEF+pPB-SV cells with cTERT. CEF+pPB-SV cells that were stored in liquid nitrogen at passage 9 were taken into culture, passaged in ACF medium and transfected at passage 11 cells with pPB-cTERT or pPB-EV in combination with the transposase expression vector. After transfection, cells were seeded and passaged. CEF+pPB-SV+pPB-EV cells stopped proliferating and died after passage 16 (data not shown). Cells transfected both with pPB-SV and pPB-cTERT continued to proliferate vigorously and were passaged until they had performed over 70 PDs (passage 33, FIG. 5).

At this point, cells were still healthy and proliferating well. Therefore, we concluded that we had established another immortalized CEF cell line. This cell line was named CEF ST-2 (for CEF+SV40 T Ag+cTERT-nr.2). CEF ST-2 cells have a fibroblastic morphology which remains constant during passaging (FIG. 6). CEF ST-2 cells of different passages have been frozen down in ampoules for liquid nitrogen storage. These cells can be easily regrown after liquid nitrogen storage.

Replication of HVT on CEF ST-1 and CEF ST-2.

We tested both the CEF ST-1 and CEF ST-2 cell line for their ability to support Herpes virus of turkey (HVT) replication. First, using an immunofluorescence assay (IF), we demonstrated that CEF ST-1 can be infected by HVT and supports the replication of HVT. CEF ST-1 cells were infected with HVT and fixed for IF after 72, 96 and 120 hours. HVT-positive foci could be seen in HVT-infected CEF ST-1 cells at all time-points, indicating that CEF ST-1 cells can be infected by HVT and support cell-to-cell spread of HVT (data not shown).

In a second experiment, we compared the efficiency of HVT infection and cell-to-cell spread between the CEF ST-1 and CEF ST-2 cells. Both CEF ST-1 and CEF ST-2 were infected with HVT and fixed at different time-points to study the kinetics of HVT replication in these cell lines. HVT-positive foci were present in both cell lines after 24, 48 and 72 hours and the number and size of the foci increased in time (data not shown). From these experiments it was clear that a higher number of HVT foci and also larger foci were seen in CEF ST-2 compared to CEF ST-1. We therefore concluded that CEF ST-2 cells are a better substrate for HVT replication than CEF ST-1.

Next, we examined HVT replication kinetics in the CEF ST-2 line in more detail. CEF ST-2 cells were infected with HVT and samples were taken 72, 96, 120 and 144 hours after infection to determine the number of plaque forming units (PFU) per ml (FIG. 7). These results indicate that HVT replicates on CEF ST-2 cells, and although differences in titer between different times of harvesting are small, virus titers seem to peak around 96 hours after infection (FIG. 7).

HVT can be Passaged on CEF ST-2 Cells.

After we had established that CEF ST-2 is a substrate for HVT infection and replication, we examined whether HVT-infected CEF ST-2 cells could infect fresh monolayers of CEF ST-2 cells. CEF ST-2 cells were infected with HVT, harvested after 96 hours and seeded onto a monolayer of fresh CEF ST-2 cells. This procedure was repeated 4 times and at each passage cells were fixed for IF staining and samples were taken to determine the number of PFU/ml. The IF staining demonstrated that HVT-positive foci were present after each passage and a large number of clear HVT foci were seen after the fourth passage (data not shown). Titration showed that HVT titers at passage 2 are slightly lower compared to passage 1 titers (FIG. 8). However, subsequent passaging on CEF ST-2 cells resulted in an increase in HVT titers with each passage and at passage 5 HVT titers were $10^{5.7}$ PFU/ml. This clearly shows that the CEF ST-2 cell line is a suitable substrate for HVT replication.

CEF ST-2 is a Substrate for Replication of Recombinant HVT Constructs.

HVT can also be used as a viral vector for the expression of antigens, e.g. of other avian viruses such as Newcastle Disease Virus (NDV), Infectious Bursal Disease virus (IBDV) or Infectious Laryingotracheitis virus (ILT)(Iqbal, 2012). To test whether CEF ST-2 cells also allow replication of recombinant HVT constructs, CEF ST-2 cells were infected either with wild type HVT, a recombinant HVT expressing both an NDV F and a IBDV VP2 antigen (HVT-NDV-IBDV) or a recombinant HVT expressing an ILT gD/gI antigen (HVT-ILT). Cells were fixed for IF staining or cells were harvested to make samples for titration 96 hours after infection. IF staining clearly showed foci both for wild type HVT and recombinant HVT constructs in CEF ST-2 cells (data not shown). Titration of the samples also demonstrated that CEF ST-2 cells support the replication of HVT recombinants (FIG. 9) although replication of the recombinant HVTs is less efficient than wild type HVT replication in the conditions used.

REFERENCE LIST

Iqbal, M. (2012). Progress toward the development of polyvalent vaccination strategies against multiple viral infections in chickens using herpesvirus of turkeys as vector. Bioengineered. 3, 222-226.

Venkatesan, R. N. and Price, C. (1998). Telomerase expression in chickens: constitutive activity in somatic tissues and down-regulation in culture. Proc. Natl. Acad. Sci. U. S. A 95, 14763-14768.

Willemse, M. J., Strijdveen, I. G., van Schooneveld, S. H., van den Berg, M. C., and Sondermeijer, P. J. (1995). Transcriptional analysis of the short segment of the feline herpesvirus type 1 genome and insertional mutagenesis of a unique reading frame. Virology 208, 704-711.

Yusa, K., Rad, R., Takeda, J., and Bradley, A. (2009). Generation of transgene-free induced pluripotent mouse stem cells by the piggyBac transposon. Nat. Methods 6, 363-369.

Yusa, K., Zhou, L., Li, M. A., Bradley, A., and Craig, N. L. (2011). A hyperactive piggyBac transposase for mammalian applications. Proc. Natl. Acad. Sci. U. S. A 108, 1531-1536.

The invention claimed is:

1. A stably transfected immortalized chicken embryo fibroblast (CEF), wherein said immortalized CEF (i) expresses an SV40 T antigen, (ii) expresses a chicken telomerase (cTERT) under the control of a heterologous promoter, and (iii) does not comprise an exogenous retroviral Long Terminal Repeat (LTR) DNA.

2. A cell culture comprising the immortalized CEF of claim 1.

3. The cell culture of claim 2, which is infected with an avian virus or avian viral vector.

4. The cell culture of claim 3, wherein the avian virus or avian viral vector is selected from the group consisting of Marek's Disease virus (MDV), the MDV-related Herpes virus of turkey (HVT), Newcastle Disease virus (NDV), Infectious Bronchitis virus (IBV), Infectious Bursal Disease virus (IBDV), Egg Drop Syndrome virus (EDSV), Turkey Rhinotracheitis virus (TRT), Reovirus (RV) and a HVT vector; wherein said HVT vector comprises an IBDV VP2-gene, an IBV-spike protein gene, an avian influenza HA gene, an ILT gD/gI protein gene, or an NDV F-gene.

5. A method of preparing the immortalized CEF of claim 1, comprising the steps of:
   a) obtaining primary CEF cells;
   b) transfecting said primary CEFs with:
      i) a first DNA molecule free of LTR sequences, comprising transposon inverted repeats and further comprising a gene encoding the SV40 T antigen under the control of a suitable promoter;
      ii) a second DNA molecule free of LTR sequences, comprising transposon inverted repeats and further comprising a gene encoding chicken telomerase (cTERT) under the control of a suitable promoter; and
      iii) a third DNA molecule comprising a gene encoding transposase under the control of a suitable promoter; and
   c) selecting CEF cells that have been cultured for at least 45 cell cycles.

6. A method of preparing the immortalized CEF of claim 1, comprising the steps of:
   a) obtaining primary CEF cells;
   b) transfecting said primary CEF cells with a single DNA molecule free of LTR sequences, comprising (i) transposon inverted repeats and a gene encoding the SV40 T antigen under the control of a suitable promoter, (ii) a gene encoding chicken telomerase under the control of a suitable promoter, and (iii) a gene encoding transposase under the control of a suitable promoter; and
   c) selecting CEF cells that have been cultured for at least 45 cell cycles.

7. A method of preparing the immortalized CEF of claim 1, comprising the steps of:
   a) obtaining primary CEF cells;
   b) transfecting said primary CEF cells with (i) a first DNA molecule free of LTR sequences, comprising transposon inverted repeats, a gene encoding the SV40 T antigen under the control of a suitable promoter, and a gene encoding chicken telomerase under the control of a suitable promoter, and (ii) a second DNA molecule comprising a gene encoding transposase under the control of a suitable promoter; and
   c) selecting CEF cells that have been cultured for at least 45 cell cycles.

8. The method of claim 5, wherein said CEF cells have been cultured for at least 100 cell cycles.

9. The method of claim 6, wherein said CEF cells have been cultured for at least 100 cell cycles.

10. The method of claim 7, wherein said CEF cells have been cultured for at least 100 cell cycles.

11. A method for replicating an avian virus or avian viral vector, wherein said method comprises the steps of:
   a) culturing the immortalized CEF of claim 1;
   b) contacting the immortalized CEF with the avian virus or avian viral vector;
   c) allowing the avian virus or avian viral vector to replicate; and
   d) isolating a progeny virus or vector from said immortalized CEF.

12. The method of claim 11, wherein the avian virus or avian viral vector is selected from the group of avian viruses consisting of Marek's Disease virus (MDV), the MDV-related Herpes virus of turkey (HVT), Newcastle Disease virus (NDV), Infectious Bronchitis virus (IBV), Infectious Bursal Disease virus (IBDV), Egg Drop Syndrome virus (EDSV), Turkey Rhinotracheitis virus (TRT), Reovirus (RV), a HVT vector; wherein said HVT vector comprises an IBDV VP2-gene, an IBV-spike protein gene, an avian influenza HA gene, an ILT gD/gI protein gene, or an NDV F-gene.

13. The method of claim 11, wherein the avian virus or avian viral vector is selected from the group of avian viruses consisting of a MDV and a MDV vector virus.

14. A method of preparing a vaccine comprising an avian virus or an avian viral vector, comprising the step of mixing the cell culture of claim 3 with a pharmaceutically acceptable carrier.

15. The method of claim 14, wherein the avian virus or an avian viral vector is an MDV.

16. The method of claim 14, wherein the MDV or MDV viral vector is in a live attenuated form.

17. A vaccine comprising the cell culture of claim 3, and a pharmaceutically acceptable carrier.

18. A method of preparing a vaccine comprising an avian virus or an avian viral vector, wherein the method comprises the steps of:
   a) infecting the cell culture of claim 2 with an avian virus or an avian viral vector;
   b) replicating said avian virus or an avian viral vector;
   c) isolating a progeny avian virus or avian viral vector; and
   d) mixing the progeny avian virus or avian viral vector with a pharmaceutically acceptable carrier.

* * * * *

SEQUENCE LISTING

```
<160> NUMBER OF SEQ ID NOS: 4

<210> SEQ ID NO 1
<211> LENGTH: 33
<212> TYPE: DNA
<213> ORGANISM: artificial sequence
<220> FEATURE:
<223> OTHER INFORMATION: PCR primer SV40 Tag 5' BII

<400> SEQUENCE: 1
ggcgagatct accatggata aagttttaaa cag                          33

<210> SEQ ID NO 2
<211> LENGTH: 30
<212> TYPE: DNA
<213> ORGANISM: artificial sequence
<220> FEATURE:
<223> OTHER INFORMATION: PCR primer SV40 Tag 3' XI

<400> SEQUENCE: 2
ggcgctcgag ttatgtttca ggttcagggg                             30

<210> SEQ ID NO 3
<211> LENGTH: 55
<212> TYPE: DNA
<213> ORGANISM: artificial sequence
<220> FEATURE:
```

<223> OTHER INFORMATION: cloning primer for cTERT+FeHV polyA signal

<400> SEQUENCE: 3
caataaacat agcatacgtt atgacatggt ctaccgcgtc ttatatgggg acgac            55

<210> SEQ ID NO 4
<211> LENGTH: 1346
<212> TYPE: PRT
<213> ORGANISM: artificial sequence
<220> FEATURE:
<223> OTHER INFORMATION: Chicken telomerase protein

<400> SEQUENCE: 4

```
Met Glu Arg Gly Ala Gln Pro Gly Val Gly Val Arg Arg Leu Arg Asn
1               5                   10                  15

Val Ala Arg Glu Glu Pro Phe Ala Ala Val Leu Gly Ala Leu Arg Gly
            20                  25                  30

Cys Tyr Ala Glu Ala Thr Pro Leu Glu Ala Phe Val Arg Arg Leu Gln
        35                  40                  45

Glu Gly Gly Thr Gly Glu Val Glu Val Leu Arg Gly Asp Asp Ala Gln
    50                  55                  60

Cys Tyr Arg Thr Phe Val Ser Gln Cys Val Val Cys Val Pro Arg Gly
65                  70                  75                  80

Ala Arg Ala Ile Pro Arg Pro Ile Cys Phe Gln Gln Leu Ser Ser Gln
                85                  90                  95

Ser Glu Val Ile Thr Arg Ile Val Gln Arg Leu Cys Glu Lys Lys Lys
            100                 105                 110

Lys Asn Ile Leu Ala Tyr Gly Tyr Ser Leu Leu Asp Glu Asn Ser Cys
        115                 120                 125

His Phe Arg Val Leu Pro Ser Ser Cys Ile Tyr Ser Tyr Leu Ser Asn
    130                 135                 140

Thr Val Thr Glu Thr Ile Arg Ile Ser Gly Leu Trp Glu Ile Leu Leu
145                 150                 155                 160

Ser Arg Ile Gly Asp Asp Val Met Met Tyr Leu Leu Glu His Cys Ala
                165                 170                 175

Leu Phe Met Leu Val Pro Pro Ser Asn Cys Tyr Gln Val Cys Gly Gln
            180                 185                 190

Pro Ile Tyr Glu Leu Ile Ser Arg Asn Val Gly Pro Ser Pro Gly Phe
        195                 200                 205

Val Arg Arg Arg Tyr Ser Arg Phe Lys His Asn Ser Leu Leu Asp Tyr
    210                 215                 220

Val Arg Lys Arg Leu Val Phe His Arg His Tyr Leu Ser Lys Ser Gln
225                 230                 235                 240

Trp Trp Lys Cys Arg Pro Arg Arg Gly Arg Val Ser Ser Arg
                245                 250                 255

Lys Arg Arg Ser His Arg Ile Gln Ser Leu Arg Ser Gly Tyr Gln Pro
            260                 265                 270

Ser Ala Lys Val Asn Phe Gln Ala Gly Arg Gln Ile Ser Thr Val Thr
        275                 280                 285

Ala Arg Leu Glu Lys Gln Ser Cys Ser Ser Leu Cys Leu Pro Ala Arg
    290                 295                 300

Ala Pro Ser Leu Lys Arg Lys Arg Asp Gly Glu Gln Val Glu Ile Thr
305                 310                 315                 320

Ala Lys Arg Val Lys Ile Met Glu Lys Glu Ile Glu Glu Gln Ala Cys
                325                 330                 335
```

```
Ser Ile Val Pro Asp Val Asn Gln Ser Ser Gln Arg His Gly Thr
                340             345                 350
Ser Trp His Val Ala Pro Arg Ala Val Gly Leu Ile Lys Glu His Tyr
            355             360             365
Ile Ser Glu Arg Ser Asn Ser Glu Met Ser Gly Pro Ser Val Val His
        370             375             380
Arg Ser His Pro Gly Lys Arg Pro Val Ala Asp Lys Ser Ser Phe Pro
385             390             395                 400
Gln Gly Val Gln Gly Asn Lys Arg Ile Lys Thr Gly Ala Glu Lys Arg
                405             410             415
Ala Glu Ser Asn Arg Arg Gly Ile Glu Met Tyr Ile Asn Pro Ile His
            420             425             430
Lys Pro Asn Arg Arg Gly Ile Glu Arg Arg Ile Asn Pro Thr His Lys
            435             440             445
Pro Glu Leu Asn Ser Val Gln Thr Glu Pro Met Glu Gly Ala Ser Ser
        450             455             460
Gly Asp Arg Lys Gln Glu Asn Pro Ala His Leu Ala Lys Gln Leu
465             470             475             480
Pro Asn Thr Leu Ser Arg Ser Thr Val Tyr Phe Glu Lys Lys Phe Leu
            485             490             495
Leu Tyr Ser Arg Ser Tyr Gln Glu Tyr Phe Pro Lys Ser Phe Ile Leu
            500             505             510
Ser Arg Leu Gln Gly Cys Gln Ala Gly Gly Arg Arg Leu Ile Glu Thr
            515             520             525
Ile Phe Leu Ser Gln Asn Pro Leu Lys Glu Gln Asn Gln Ser Leu
530             535             540
Pro Gln Gln Lys Trp Arg Lys Lys Arg Leu Pro Lys Arg Tyr Trp Gln
545             550             555             560
Met Arg Glu Ile Phe Gln Lys Leu Val Lys Asn His Glu Lys Cys Pro
                565             570             575
Tyr Leu Val Phe Leu Arg Lys Asn Cys Pro Val Leu Leu Ser Glu Ala
            580             585             590
Cys Leu Lys Lys Thr Glu Leu Thr Leu Gln Ala Ala Leu Pro Gly Glu
            595             600             605
Ala Lys Val His Lys His Thr Glu His Gly Lys Glu Ser Thr Glu Gly
            610             615             620
Thr Ala Pro Asn Ser Phe Leu Ala Pro Pro Ser Val Leu Ala Cys Gly
625             630             635             640
Gln Pro Glu Arg Gly Glu Gln His Pro Ala Glu Gly Ser Asp Pro Leu
                645             650             655
Leu Arg Glu Leu Leu Arg Gln His Ser Ser His Trp Gln Val Tyr Gly
            660             665             670
Phe Val Arg Glu Cys Leu Glu Arg Val Ile Pro Ala Glu Leu Trp Gly
            675             680             685
Ser Ser His Asn Lys Cys Arg Phe Phe Lys Asn Val Lys Ala Phe Ile
            690             695             700
Ser Met Gly Lys Tyr Ala Lys Leu Ser Leu Gln Gln Leu Met Trp Lys
705             710             715             720
Met Arg Val Asn Asp Cys Val Trp Leu Arg Leu Ala Lys Gly Asn His
                725             730             735
Ser Val Pro Ala Tyr Glu His Cys Tyr Arg Glu Glu Ile Leu Ala Lys
            740             745             750
Phe Leu Tyr Trp Leu Met Asp Ser Tyr Val Ile Glu Leu Leu Lys Ser
```

-continued

```
              755                 760                 765
Phe Phe Tyr Ile Thr Glu Thr Met Phe Gln Lys Asn Met Leu Phe Tyr
        770                 775                 780

Tyr Arg Lys Phe Ile Trp Gly Lys Leu Gln Asn Ile Gly Ile Arg Asp
785                 790                 795                 800

His Phe Ala Lys Val His Leu Arg Ala Leu Ser Ser Glu Glu Met Glu
                805                 810                 815

Val Ile Arg Gln Lys Lys Tyr Phe Pro Ile Ala Ser Arg Leu Arg Phe
                820                 825                 830

Ile Pro Lys Met Asn Gly Leu Arg Pro Val Val Arg Leu Ser Arg Val
                835                 840                 845

Val Glu Gly Gln Lys Leu Ser Lys Glu Ser Arg Glu Lys Lys Ile Gln
850                 855                 860

Arg Tyr Asn Thr Gln Leu Lys Asn Leu Phe Ser Val Leu Asn Tyr Glu
865                 870                 875                 880

Arg Thr Val Asn Thr Ser Ile Ile Gly Ser Ser Val Phe Gly Arg Asp
                885                 890                 895

Asp Ile Tyr Arg Lys Trp Lys Glu Phe Val Thr Lys Val Phe Glu Ser
                900                 905                 910

Gly Gly Glu Met Pro His Phe Tyr Phe Val Lys Gly Asp Val Ser Arg
                915                 920                 925

Ala Phe Asp Thr Ile Pro His Lys Lys Leu Val Glu Val Ile Ser Gln
                930                 935                 940

Val Leu Lys Pro Glu Ser Gln Thr Val Tyr Gly Ile Arg Trp Tyr Ala
945                 950                 955                 960

Val Ile Met Ile Thr Pro Thr Gly Lys Ala Arg Lys Leu Tyr Lys Arg
                965                 970                 975

His Val Ser Thr Phe Glu Asp Phe Ile Pro Asp Met Lys Gln Phe Val
                980                 985                 990

Ser Lys Leu Gln Glu Arg Thr Ser Leu Arg Asn Ala Ile Val Val Glu
                995                 1000                1005

Gln Cys Leu Thr Phe Asn Glu Asn Ser Ser Thr Leu Phe Thr Phe
        1010                1015                1020

Phe Leu Gln Met Leu His Asn Asn Ile Leu Glu Ile Gly His Arg
        1025                1030                1035

Tyr Tyr Ile Gln Cys Ser Gly Ile Pro Gln Gly Ser Ile Leu Ser
        1040                1045                1050

Thr Leu Leu Cys Ser Leu Cys Tyr Gly Asp Met Glu Asn Lys Leu
        1055                1060                1065

Leu Cys Gly Ile Gln Lys Asp Gly Val Leu Ile Arg Leu Ile Asp
        1070                1075                1080

Asp Phe Leu Leu Val Thr Pro His Leu Met Gln Ala Arg Thr Phe
        1085                1090                1095

Leu Arg Thr Ile Ala Ala Gly Ile Pro Glu Tyr Gly Phe Leu Ile
        1100                1105                1110

Asn Ala Lys Lys Thr Val Val Asn Phe Pro Val Asp Asp Ile Pro
        1115                1120                1125

Gly Cys Ser Lys Phe Lys His Leu Pro Asp Cys Arg Leu Ile Ser
        1130                1135                1140

Trp Cys Gly Leu Leu Leu Asp Val Gln Thr Leu Glu Val Tyr Cys
        1145                1150                1155

Asp Tyr Ser Ser Tyr Ala Phe Thr Ser Ile Arg Ser Ser Leu Ser
        1160                1165                1170
```

-continued

```
Phe Asn Ser Ser Arg Ile Ala Gly Lys Asn Met Lys Cys Lys Leu
    1175                1180            1185

Thr Ala Val Leu Lys Leu Lys Cys His Pro Leu Leu Leu Asp Leu
    1190            1195            1200

Lys Ile Asn Ser Leu Gln Thr Val Leu Ile Asn Ile Tyr Lys Ile
    1205            1210            1215

Phe Leu Leu Gln Ala Tyr Arg Phe His Ala Cys Val Leu Gln Leu
    1220            1225            1230

Pro Phe Asn Gln Lys Val Arg Asn Asn Pro Asp Phe Phe Leu Arg
    1235            1240            1245

Ile Ile Ser Asp Thr Ala Ser Cys Cys Tyr Phe Ile Leu Lys Ala
    1250            1255            1260

Lys Asn Pro Gly Val Ser Leu Gly Ser Lys Asp Ala Ser Gly Met
    1265            1270            1275

Phe Pro Phe Glu Ala Ala Glu Trp Leu Cys Tyr His Ala Phe Ile
    1280            1285            1290

Val Lys Leu Ser Asn His Lys Val Ile Tyr Lys Cys Leu Leu Lys
    1295            1300            1305

Pro Leu Lys Val Tyr Lys Met His Leu Phe Gly Lys Ile Pro Arg
    1310            1315            1320

Asp Thr Met Glu Leu Leu Lys Thr Val Thr Glu Pro Ser Leu Cys
    1325            1330            1335

Gln Asp Phe Lys Thr Ile Leu Asp
    1340            1345
```